(12) United States Patent
Miesner et al.

(10) Patent No.: US 9,510,730 B2
(45) Date of Patent: Dec. 6, 2016

(54) IMAGING METHOD AND APPARATUS

(71) Applicants: Optiscan Pty Ltd., Notting Hill (AU); Carl Zeiss Surgical GmbH, Oberkochen (DE); Carl Zeiss Meditec Inc., Dublin, CA (US)

(72) Inventors: Hans-Joachim Miesner, Aalen (DE); Christoph Hauger, Aalen (DE); Werner Nahm, Buehlerzell (DE); Frank Rudolph, Aalen (DE); Guido Hattendorf, Phoenix, AZ (US); Peter M. Delaney, Carnegie (AU); John D. Allen, Essendon (AU)

(73) Assignees: Optiscan Pty Ltd., Victoria (AU); Carl Zeiss Meditec AG, Jena (DE); Carl Zeiss Meditec Inc., Dublin, CA (US)

( * ) Notice: Subject to any disclaimer, the term of this patent is extended or adjusted under 35 U.S.C. 154(b) by 0 days.

(21) Appl. No.: 14/228,896

(22) Filed: Mar. 28, 2014

(65) Prior Publication Data
US 2015/0073270 A1     Mar. 12, 2015

Related U.S. Application Data

(63) Continuation of application No. 12/756,692, filed on Apr. 8, 2010, now abandoned.
(Continued)

(51) Int. Cl.
*A61B 1/04*     (2006.01)
*A61B 1/07*     (2006.01)
(Continued)

(52) U.S. Cl.
CPC ......... *A61B 1/00078* (2013.01); *A61B 1/0005* (2013.01); *A61B 1/0008* (2013.01); *A61B 1/00009* (2013.01); *A61B 1/00041* (2013.01); *A61B 1/00045* (2013.01); *A61B 1/042* (2013.01); *A61B 1/06* (2013.01); *A61B 1/227* (2013.01); *A61B 1/233* (2013.01);
(Continued)

(58) Field of Classification Search
CPC ............................. A61B 1/07; A61B 1/00045
USPC .................................................. 600/101, 128
See application file for complete search history.

(56) References Cited

U.S. PATENT DOCUMENTS 4,562,831 A * 1/1986 Murakoshi ............... A61B 1/05
                                                    348/70
5,999,837 A * 12/1999 Messner et al. .............. 600/407
(Continued)

*Primary Examiner* — W B Perkey
(74) *Attorney, Agent, or Firm* — Alston & Bird LLP

(57) ABSTRACT

An imaging apparatus and method are provided. The probe for an imaging apparatus includes a manually manipulable proximal portion; a straight distal portion with a distal tip for locating at a site to define an observational field; and a curved portion between the proximal portion and the distal portion. The imaging method includes the steps of locating a distal tip of an imaging probe at a site to define an observational field; irradiating the observational field from the distal tip; and collecting a return signal at the distal tip; wherein the probe comprises a manually manipulable proximal portion. The apparatus and method provided herein are useful for various applications including but not limited to endomicroscopy and other microsurgical procedures performed under optical stereoscopic magnified visualization, such as neurosurgery, ENT/facial surgery and spinal surgery.

18 Claims, 2 Drawing Sheets

Related U.S. Application Data

(60) Provisional application No. 61/212,272, filed on Apr. 8, 2009.

(51) Int. Cl.
 *A61B 1/00* (2006.01)
 *A61B 7/02* (2006.01)
 *A61B 1/313* (2006.01)
 *A61B 5/00* (2006.01)
 *A61B 5/06* (2006.01)
 *G02B 21/00* (2006.01)
 *G02B 23/24* (2006.01)
 *A61B 1/06* (2006.01)
 *A61B 1/227* (2006.01)
 *A61B 1/233* (2006.01)
 *A61B 1/267* (2006.01)
 *A61B 8/12* (2006.01)

(52) U.S. Cl.
 CPC .............. *A61B 1/267* (2013.01); *A61B 1/313* (2013.01); *A61B 5/0066* (2013.01); *A61B 5/0068* (2013.01); *A61B 5/0075* (2013.01); *A61B 5/0084* (2013.01); *A61B 5/064* (2013.01); *A61B 5/065* (2013.01); *A61B 5/6835* (2013.01); *A61B 5/6852* (2013.01); *A61B 5/6855* (2013.01); *A61B 7/02* (2013.01); *A61B 8/12* (2013.01); *A61B 90/90* (2016.02); *A61B 90/92* (2016.02); *A61B 90/94* (2016.02); *G02B 21/0028* (2013.01); *G02B 23/2476* (2013.01); *A61B 1/00172* (2013.01)

(56) References Cited

U.S. PATENT DOCUMENTS

| | | | | |
|---|---|---|---|---|
| 6,389,205 | B1* | 5/2002 | Muckner et al. | 385/117 |
| 6,661,571 | B1* | 12/2003 | Shioda et al. | 359/372 |
| 7,585,273 | B2* | 9/2009 | Adler et al. | 600/117 |
| 7,783,133 | B2* | 8/2010 | Dunki-Jacobs | A61B 1/04 382/100 |
| 7,867,169 | B2* | 1/2011 | Webler et al. | 600/463 |
| 2005/0020877 | A1* | 1/2005 | Ishihara et al. | 600/109 |
| 2005/0027167 | A1* | 2/2005 | Chatenever | A61B 1/042 600/173 |
| 2005/0228230 | A1* | 10/2005 | Schara | A61B 1/00045 600/171 |
| 2006/0211918 | A1* | 9/2006 | Lieponis | 600/182 |
| 2008/0319290 | A1* | 12/2008 | Mao et al. | 600/323 |
| 2011/0166420 | A1* | 7/2011 | Miesner et al. | 600/160 |
| 2011/0178395 | A1* | 7/2011 | Miesner et al. | 600/425 |

* cited by examiner

IMAGING METHOD AND APPARATUS

CROSS REFERENCE TO RELATED APPLICATIONS

This application is a continuation application of U.S. application Ser. No. 12/756,692 filed Apr. 8, 2010, which claims the benefit of U.S. Provisional Patent Application No. 61/212,272 filed Apr. 8, 2009, the entire contents of all of which are hereby incorporated herein by reference.

FIELD OF THE INVENTION

The present invention relates generally to an imaging method and apparatus, of particular but by no means exclusive application in endomicroscopy and in microsurgical and other procedures performed under optical stereoscopic magnified visualization, including neurosurgery, ENT/facial surgery and spinal surgery.

BACKGROUND OF THE INVENTION

One existing microscopic probe comprises an endoscope or endomicroscope, with an endoscopic head for insertion into a patient (through the mouth or anus) coupled to a laser source by an optical fibre or optical fibre bundle. Another microscopic probe is similar to this endoscope, but adapted for examining the skin.

SUMMARY OF THE INVENTION

According to a first aspect of the invention, therefore, there is provided a probe for an imaging apparatus, comprising: a manually manipulable proximal portion; a straight distal portion with a distal tip for locating at a site to define an observational field; and a curved portion between the proximal portion and the distal portion; wherein the straight portion has a length of between 75 mm to 205 mm, the curved portion provides an angle between the proximal portion and the distal portion of between 120° and 150°, and the probe has a working length of between 125 mm to 300 mm. In certain particular embodiments, the curved portion provides an angle between the proximal portion and the distal portion of between 130° and 140°, and in a specific embodiment, the angle is approximately 135°. The probe may be an endoscopic probe, such as a confocal endoscopic probe. The probe may be, for example, a neurological probe, an ENT probe, an ultrasound probe, an OCT probe or a CARS probe.

It will be appreciated by those in the art that the distal tip refers to the terminal portion of the probe, and assumes different forms in each of these embodiments. For example, the distal tip of the ultrasound probe comprises an ultrasound head. The probe may have an orientation marking that allows identification of an orientation of the probe. The invention also provides an imaging apparatus, comprising the probe described above.

The apparatus may comprise an endomicroscope or other endomicroscopic apparatus. An endomicroscope is high resolution microscope capable of cellular, subcellular and surface and subsurface imaging, such as a miniature confocal microscope or other scanning microscope probe. The apparatus may be adapted to be used with a macroscopic visualization apparatus such as an operating microscope. As will be understood by those in the art, an operating microscope is the main visualization tool of a microsurgeon. It provides high magnification of tissue and thus allows very fine surgical procedures to be performed, though does not achieve cellular or subcellular resolution. An operating microscope is typically a direct viewing binocular device with a continuous passive optical path from tissue to observer. Thus, while an operating microscope is commonly referred to as a 'microscope', it should not be confused with an endomicroscope or an apparatus according to the present invention, which are specific types of microscopes that operate with at least an order of magnitude higher magnification than an operating microscope. The apparatus may be configured to orient an image collected with the probe so as to correspond to a normal field of view of a macroscopic visualization apparatus. The invention also provides an operating microscope that includes an imaging apparatus as described above.

According to a second aspect of the invention, therefore, there is provided an imaging method, comprising: locating a distal tip of an imaging probe at a site to define an observational field; irradiating the observational field from the distal tip; and collecting a return signal at the distal tip; wherein the probe comprises a manually manipulable proximal portion, a straight distal portion including the distal tip, and a curved portion between the proximal portion and the distal portion, and wherein the straight portion has a length of between 75 mm to 205 mm, the curved portion provides an angle between the proximal portion and the distal portion of between 120° and 150°, and the probe has a working length of between 125 mm to 300 mm.

In certain particular embodiments, the angle between the proximal portion and the distal portion is between of between 130° and 140°, and in a specific embodiment, the angle is approximately 135°. The probe may be an endoscopic probe, in which case the observational field is irradiated with light emitted from the distal tip, and the return signal comprises return light.

BRIEF DESCRIPTION OF THE DRAWINGS

In order that the invention may be more clearly ascertained, preferred embodiments will now be described, by way of example only, with reference to the accompanying drawing, in which.

DETAILED DESCRIPTION OF THE EMBODIMENTS

Figure 1:
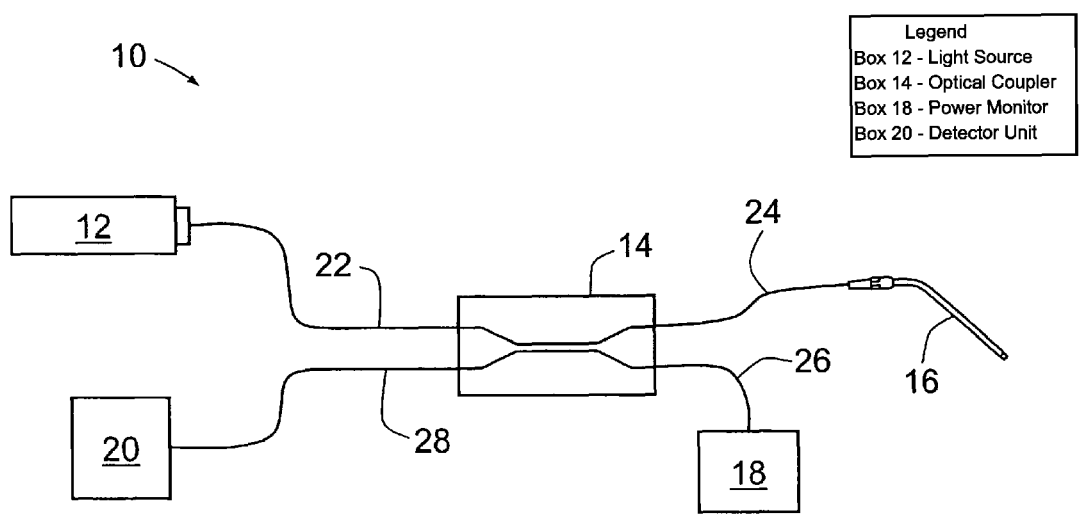
FIG. 1 is a schematic view of a confocal endomicroscopic apparatus according to an embodiment of the present invention.

FIG. 1 is a schematic view of an endomicroscope system 10 according to an embodiment of the present invention. System 10 includes a laser source 12 with 488 nm wavelength output, a light separator in the form of an optical coupler 14, a confocal endomicroscope probe 16, a power monitor 18 and a detection unit 20. System 10 includes a control box (not shown) that houses laser source 12 and detection unit 20 (in the form of a photomultiplier tube), and a computer (not shown) for receiving, storing and displaying data from detection unit 20. Probe 16 includes an x-y scanning mechanism (not shown) so that light emitted by probe 16 has a point observational field that is scanned in a raster scan so that an image of the observational field—comprising a portion of a sample—can be collected and displayed. System 10 therefore also includes electrical cables for transmitting a scanning signal from the aforementioned control box to probe 16, for powering the scanning mechanism.

In use, laser light from source 12 is transmitted by first optical fibre 22 to optical coupler 14; a first portion of the light is coupled into second optical fibre 24 and transmitted to probe 16. A second portion of the light is coupled into third optical fibre 26 and transmitted to power monitor 18. Probe 16 is adapted to be manipulated manually and placed against a sample to be imaged confocally. Before or during such imagining, the power deposited onto the sample can be monitored with power monitor 18 and the known ratio between the power coupled by optical coupler 14 into second fibre 24 and that into third fibre 26. Light returned confocally by the sample and collected by probe 16 is transmitted back to optical coupler 14 and a portion of that return light is then coupled into fourth or return optical fibre 28 and transmitted to detection unit 20. An image can then be constructed from the light detected by detection unit 20 and the aforementioned scanning signal, as the latter allows the origin within the sample of the return light to be ascertained. All the optical fibres 22, 24, 26, 28 are single moded at the wavelength of laser source 12, though in some embodiments few- or multi-moded fibre may be used for fourth optical fiber 28.

Figure 2:
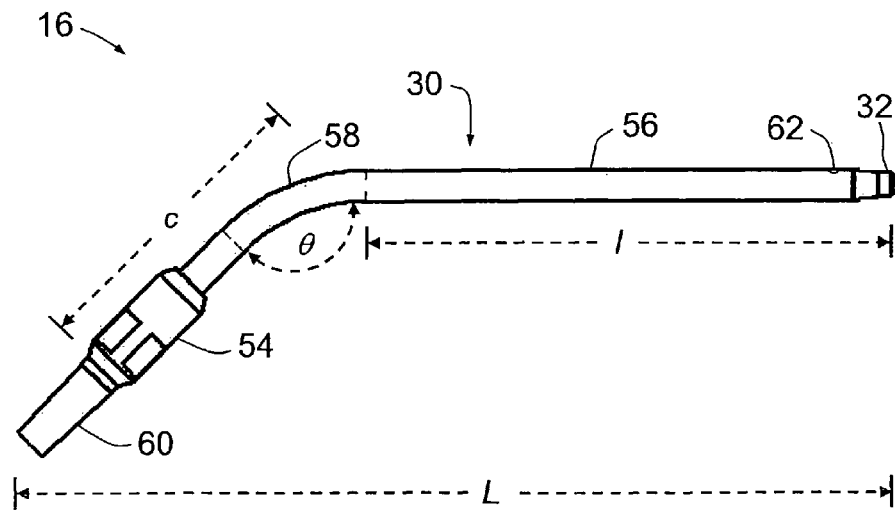
FIG. 2 is a schematic view of the probe of the apparatus of FIG. 1.
Figure 3:
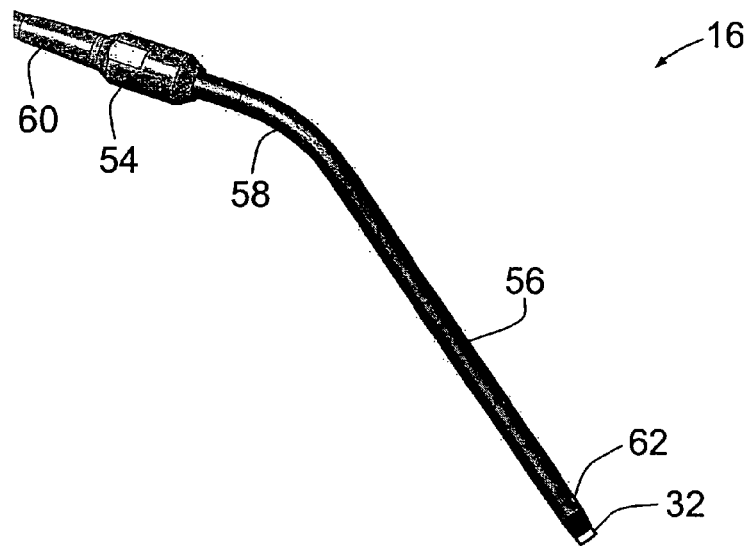
FIG. 3 is a schematic, perspective view of the probe of the apparatus of FIG. 1.

Probe 16 is shown in greater detail in FIGS. 2 and 3, and comprises a rigid steel housing 30 with a distal tip 32 adapted to be placed gently into contact with the sample. Housing 30 houses the terminal portion of second optical fibre 24, the scanning mechanism for scanning the exit tip of second optical fibre 24, and an optical train for receiving the scanned light from the exit tip of second optical fibre 24 and focusing it onto or into the sample.

Figure 4:
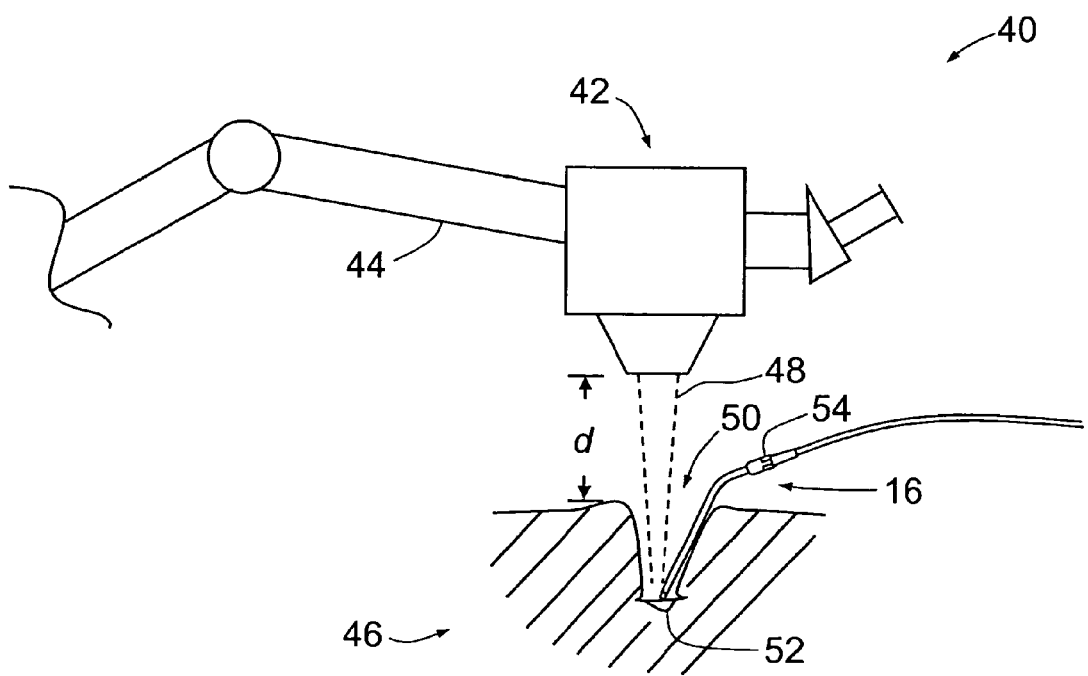
FIG. 4 is a schematic view of the probe of the apparatus of FIG. 1 in use.

System 10 is configured to be used with an operating microscope as is illustrated schematically at 40 in FIG. 4. In use, a macroscopic visualization apparatus in the form of operating microscope 42 is supported by arm 44 above a subject 46, and defines an optical corridor 48 into an access corridor 50 created in the subject 46 to provide access to a site or sample 52 under examination. Probe 16, once in position against sample 52, can be viewed with operating microscope 42.

Probe 16 is adapted to allow easy fine control of its distal tip 32 by manual 15 manipulation of a proximal portion 54 while distal tip 32 is viewed by operating microscope 42, without probe 16 significantly obstructing optical corridor 48. Probe 16 is thus adapted to be supported comfortably by a user for accessing sample 52 through access corridor 50, and—referring to FIG. 2—has an insertable and essentially straight distal insertion portion 56 with a length 1 of 75 to 205 mm (and, in the illustrated embodiment, approximately 110 mm) and an outside diameter of approximately 6.6 mm. Proximal portion 54 of probe 16 and insertion portion 56 are coupled by a curved portion 58, which provides approximately a 45° bend between those two portions, so that the angle θ between proximal portion 54 and insertion portion 56 is approximately 135°. Curved portion 58 allows distal tip 32 of probe 16 to be placed at sample 52 with manually manipulated proximal portion 54 held just outside access corridor 50, without proximal portion 54 being in optical corridor 48. Curved portion 58 thus allows the user to have a line of sight through operating microscope 42 along insertion portion 56 of probe 16 that is unobstructed by the user's hands.

In use, insertion of probe 16 into access corridor 50 is accomplished while operating microscope 42 is in place over access corridor 50 and, therefore, probe 16 is dimensioned to fit within the available working distances. For example, for a operating microscope 42 set at a 500 mm working distance and 35 arranged to focus on the deepest structures in an access corridor 50 of 200 mm depth, probe 16 should have a minimum reach of just over 200 mm (and, in practice, no less than 205 mm), provided by insertion portion 56. However, this leaves an access working distance (i.e. between subject 46 and operating microscope 42) d of only 300 mm. Hence, insertion portion 56 (of ≥205 mm), curved portion 58, proximal portion 54 and cable relief 60 should preferably be accommodated by this 300 mm, that is, have a "working length" (i.e. length in a direction parallel to insertion portion 56) of 300 mm. This defines the longest probe dimensions generally usable in this scenario.

In applications where higher magnifications of operating microscope 42 are employed, probe 16 should accommodate shorter working distances. This may 10 involve working at a distance of 200 mm from sample 52, with sample 52 up to 70 mm deep. In this situation the minimum length of insertion portion 56 would be 75 mm and the total length of probe 16 less than 125 mm to allow probe 16 to be located in the working distance of 125 mm between the subject 46 and operating microscope 42.

Thus the dimensions of probe 16 comprise or depend on the following:
1) insertion portion 56: 75 mm to 205 mm;
2) working length L measured in direction of insertion portion 56: 125 mm to 300 mm;
3) handheld, proximal portion 54, is adapted to sit at a comfortable angle for the position of the user's hand (extending from the bridge between the thumb and index finger to the tips of thumb and index finger);
4) angle θ provided by curved portion 58: between 120° and 150° (and preferably between 130° and 140°, and in this embodiment approximately 135°) 25 between insertion portion 56 and handheld, proximal portion 54;
5) the combined length c of proximal portion 54 and the outer surface of curved portion 58 (together being that part of probe 16 likely to be manipulated by the user during use), in a direction parallel with proximal portion 54, should not be less than the length required for the user to grip probe 16 along this combined length with a minimal number of fingers, while leaving a clear line of sight along the insertion portion 56; this minimum length is estimated to be about 59 mm;
6) combined length c depends on the balance of probe 16 and the available working space: probe 16 should not be unduly heavy in its balance point in respect to the bend; it is estimated that combined length c should not be greater than 75% of the length of the insertion portion 56.

In addition, probe 16 is provided with orientation marking on insertion portion 56, close to distal tip 32, to allow orientation of the ultimate image relative to the field visualized by operating microscope 42. The orientation marking, in the present embodiment, comprises a dot 62 close to distal tip 32, representing "up" in the microscopic field. In other embodiments, however, the orientation 5 marking comprises:
1) a plurality of visually distinguishable dots distributed around insertion portion 56;
2) axially oriented stripes indicating each quadrant ("north/south/east/west" markings);

3) nearly radial markings oriented at an angle to the axis of the scope with the angle being different in different quadrants so that observation from any side enables recognition of which side is being viewed;
4) colour coded markings (such as a plurality of dots, stripes or radial markings) to enhance the differences between different quadrants.

The orientation marking may also comprise any combination of these that serves to allow the identification of the orientation of probe 16.

System 10 orients its output of images collected with probe 16 to correspond to the normal field of view of operating microscope 42, by aligning the "up" direction in that field of view (i.e. typically away from the user) and the top of an image collected with probe 16 when probe 16 is held in a relaxed, neutral manner. Hence, "up" in the confocal image is oriented so that advancing the arm in the direction of the user's forearm with straight wrist will move probe 16 "up" relative to the image. Swinging the arm right from the elbow with straight wrist would move probe 16 right relative to the displayed image, etc.

The optical path for the left and right eye through operating microscope 42 defines a coordinate system for up/down/left/right orientation of the user. The integrated camera of operating microscope 42 can thus be used to measure the outer orientation of probe 16 according to this coordinate system. The orientation of an image generated by system 10 can then be transformed to be correctly oriented to the coordinate system of operating microscope 42. This can be done by rotating the endoscopic image, so that up/down/right/left 35 directions coincide with the coordinate system of operating microscope 42. Alternatively, the image orientation of the endoscopic image can be adjusted to the coordinate system of the microscope by transforming the input signals for the scanning mechanism of system 10, that is, by rotating the two axes of the scanning mechanism.

Modifications within the scope of the invention may be readily effected by those 5 skilled in the art. It is to be understood, therefore, that this invention is not limited to the particular embodiments described by way of example hereinabove.

In the claims that follow and in the preceding description of the invention, except where the context requires otherwise owing to express language or necessary implication, the word "comprise" or variations such as "comprises" or "comprising" is used in an inclusive sense, i.e. to specify the presence of the stated features but not to preclude the presence or addition of further features in various embodiments of the invention. Further, any reference herein to prior art is not intended to imply that such prior 15 art forms or formed a part of the common general knowledge.

What is claimed is:

1. An imaging apparatus, comprising:
   a probe, comprising:
      a manually manipulable proximal portion;
      a straight distal portion coupled to a distal tip, wherein the distal tip locates and defines an observational field of a sample to be imaged confocally;
      a curved portion between the proximal portion and the straight distal portion;
      wherein the straight distal portion has a length of between 75 mm to 205 mm, and the curved portion provides an angle between the proximal portion and the straight distal portion of between 120° and 150; and
      a scanning mechanism that performs a raster scan on the observation field;
   an optical coupler that receives light from a light source and separates the received light into a first light and a second light;
   a first connection to send the first light from the optical coupler to the probe;
   a second connection to send the second light from the optical coupler to a power monitor, wherein an amount of power output to the sample is calculated based on a ratio between power coupled by the optical coupler into the first connection and power coupled by the optical coupler into the second connection; and
   a detection unit that receives a portion of light returned confocally by the sample and collected by the probe,
   wherein an image of the sample is constructed based at least in part on the portion of light detected by the detection unit and the raster scan of the observational field.

2. The imaging apparatus as claimed in claim 1, wherein the curved portion provides an angle between the proximal portion and the distal portion of between 130° and 140°.

3. The imaging apparatus as claimed in claim 1, wherein the probe is an endoscopic probe.

4. The imaging apparatus as claimed in claim 1, wherein the probe is a neurological probe, an ENT probe, an ultrasound probe, an OCT probe or a CARS probe.

5. The imaging apparatus as claimed in claim 1, comprising an orientation marking that allows identification of an orientation of the probe.

6. The imaging apparatus as claimed in claim 5, wherein the orientation marking comprises one or more dots, strips, radial markings or near radial markings.

7. The imaging apparatus as claimed in claim 5, wherein the orientation marking comprises a plurality of portions of different colours.

8. The imaging apparatus as claimed in claim 1, comprising an endomicroscopic apparatus wherein the imaging apparatus is an endomicroscopic imaging apparatus.

9. The imaging apparatus as claimed in claim 1, configured to orient an image collected with the probe so as to correspond to a normal field of view of a macroscopic visualization apparatus.

10. The imaging apparatus as claimed in claim 1, configured to orient and rotate an image collected with the probe so as to correspond to a field of view of a macroscopic visualization apparatus.

11. The imaging apparatus as claimed in claim 1, configured to orient and rotate an image collected with the probe so as to correspond to a field of view of a macroscopic visualization apparatus by transforming input signals for a scanning mechanism of the apparatus to rotate x and y axes of the scanning mechanism.

12. An imaging method, comprising:
   a probe comprising a manually manipulable proximal portion, a straight distal portion including a distal tip, and a curved portion between the proximal portion and the straight distal portion, wherein the straight distal portion has a length of between 75 mm to 205 mm, and the curved portion provides an angle between the proximal portion and the straight distal portion of between 120° and 150°;
   defining an observational field of a sample to be imaged confocally based on the location of a distal tip;
   performing a raster scan of the defined observational field;
   receiving a return signal from the distal tip containing data corresponding to the observational field;
   receiving, by an optical coupler, light from a light source;

separating, by the optical coupler, the received light into a first light and a second light;

sending, by a first connection, the first light from the optical coupler to the probe;

sending, by a second connection, the second light from the optical coupler to a power monitor, wherein an amount of power output to the sample is calculated based on a ratio between power coupled by the first connection and the second connection;

receiving, by a detection unit, a portion of light returned confocally by the sample and collected by the probe; and constructing an image of the sample based at least in part on the portion of light detected by the detection unit and the raster scan of the observational field.

13. The imaging method as claimed in claim 12, including providing an angle between the proximal portion and the distal portion of between 130° and 140°.

14. The imaging apparatus as claimed in claim 1, wherein the probe has a working length of between 125 mm to 300 mm.

15. The imaging apparatus as claimed in claim 1, wherein the curved portion provides an angle between the proximal portion and the distal portion of approximately 135°.

16. The imaging apparatus as claimed in claim 1, wherein the straight distal portion has a length of 110 mm.

17. The imaging apparatus as claimed in claim 1, wherein the straight distal portion has a length of 75 mm.

18. The imaging apparatus as claimed in claim 1, wherein the raster scan indicates an origin of the sample of the return light.

* * * * *